US006365375B1

(12) United States Patent
Dietmaier et al.

(10) Patent No.: US 6,365,375 B1
(45) Date of Patent: Apr. 2, 2002

(54) METHOD OF PRIMER-EXTENSION PREAMPLIFICATION PCR

(76) Inventors: Wolfgang Dietmaier, Annahofstr 27, D-93049 Regensburg (DE); Josef Ruschoff, Queralee 45, D-34119 Kassel (DE)

( * ) Notice: Subject to any disclaimer, the term of this patent is extended or adjusted under 35 U.S.C. 154(b) by 0 days.

(21) Appl. No.: 09/270,933

(22) Filed: Mar. 16, 1999

(51) Int. Cl.[7] .............................. C12P 19/34; C12Q 1/68
(52) U.S. Cl. ...................... 435/91.1; 435/91.2; 435/6
(58) Field of Search ................ 435/91.2, 91.1, 435/6

(56) References Cited

U.S. PATENT DOCUMENTS 5,556,772 A * 9/1996 Sorge et al. ............. 435/91.2
5,846,721 A * 12/1998 Soares et al. ................ 435/6

OTHER PUBLICATIONS

Zhang et al. Whole genome amplification from a single cell: implications for genetic analysis, Proc, Natl. Acad. Sci. USA, vol. 89, p. 5847–5851, 1992.*

Torres et al. A rapid and gentle method for isolation of genomic DNA from pathogenic nocardia spp., Clinical and Diagnostic Laboratory Immunology, 1996, vol. 3(5), p. 601–604.*

* cited by examiner

Primary Examiner—W. Gary Jones
Assistant Examiner—Joyce Tung
(74) Attorney, Agent, or Firm—Pennie & Edmonds LLP

(57) ABSTRACT

The invention provides a method for the amplification of nucleic acid fragments from a sample that comprises two or three thermocyclic amplification reactions, whereby completely randomized primers are used in the first amplification reaction and specific primers are used in the second amplification reaction, characterized in that, to amplify the DNA, a mixture of at least two DNA polymerases is used, at least one of which possesses proofreading activity. Using this method, DNA from single cells or cell clones with a low cell count can be used in mutation analysis.

5 Claims, 8 Drawing Sheets

D2S123

*Number of cells per Rct.:*   1    5

D2S123

*Number of cells per Rct.:*   10    100

SEQUENCE LISTING

<160> NUMBER OF SEQ ID NOS: 17

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Primer for
      Human Genomic Sequence

<400> SEQUENCE: 1

-continued ggttggccaa tctactccca gg                                              22

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Primer for
      Human Genomic Sequence

<400> SEQUENCE: 2
gctcactcag tgtggcaaag                                                 20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer for
      Human Genomic Sequence

<400> SEQUENCE: 3
aaacaggatg cctgccttta                                                 20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer for
      Human Genomic Sequence

<400> SEQUENCE: 4
ggactttcca cctatgggac                                                 20

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Primer for
      Human Genomic Sequence

<400> SEQUENCE: 5
aaaggcctcc cctgct                                                     16

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Primer for
      Human Genomic Sequence

<400> SEQUENCE: 6
gagcagtaag gagatt                                                     16

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Primer for
      Human Genomic Sequence

<400> SEQUENCE: 7
ctcccctgct tgcca                                                      15

```
<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Primer for
      Human Genomic Sequence

<400> SEQUENCE: 8
gatgggtagt agtatg                                                      16

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Primer for
      Human Genomic Sequence

<400> SEQUENCE: 9
gacaggtaga cctgat                                                      16

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Primer for
      Human Genomic Sequence

<400> SEQUENCE: 10
tctgaggcat aactgc                                                      16

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Primer for
      Human Genomic Sequence

<400> SEQUENCE: 11
agacctgatt tccttac                                                     17

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Primer for
      Human Genomic Sequence

<400> SEQUENCE: 12
taactgcacc cttggtc                                                     17

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Primer for
      Human Genomic Sequence

<400> SEQUENCE: 13
actgaatata aacttgtggt agttggacct                                       30
```

```
<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer for
      Human Genomic Sequence

<400> SEQUENCE: 14
tcaaagaatg gtcctgcacc                                                      20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer for
      Human Genomic Sequence

<400> SEQUENCE: 15
tcaaagaatg gtcctggacc                                                      20

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Primer for
      Human Genomic Sequence

<400> SEQUENCE: 16
ggcattcctg aagctgacag c                                                    21

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Primer for
      Human Genomic Sequence

<400> SEQUENCE: 17
ctccatgatg ctgcttacat gtc                                                  23
```

METHOD OF PRIMER-EXTENSION PREAMPLIFICATION PCR

The present application claims priority to German Patent Application No. 198 13 317.0, filed Mar. 26, 1998.

BACKGROUND OF THE INVENTION

1. Field of the Invention

The invention provides an improved method of "whole genome amplification" (WGA) that is suitable for performing DNA analysis starting with just one or a few cells. The improvement of the method basically lies in the fact that, to amplify the DNA, a mixture of two DNA polymerases is used, at least one of which possesses 3'–5' exonuclease activity.

2. Description of Related Art

WGA methods are especially important in the field of differential tumor diagnostics. The goal of differential tumor diagnostics at the molecular level is to analyze nucleic acid samples from single cells or cell populations that contain no non-malignant cells (Emmert-Buck et al., 1996; Böhm and Wielang, 1997). To obtain the appropriate samples, therefore, cell sorting methods (Abeln et al., 1994, Barret et al., 1996), microdissection methods (Shibata et al., 1992, Shibata et al., 1993, Emmert-Buck et al., 1994, Noguchi et al., 1994, Zhuang et al., 1995, Böhm et al., 1997), and laser microdissection (Schütze and Clement-Sengewald, 1994) are used with increasing frequency.

Especially sensitive methods of nucleic acid amplification are required before a molecular analysis of single cells or populations of a few cells can be performed, however. According to the prior art, methods of "whole genome amplification" (WGA) are especially well-suited for this application. These are methods that comprise two consecutive amplification reactions. The first amplification reaction is carried out using randomized primers, and the second amplification is carried out using specific primers. WGA can be used, for instance, to diagnose hereditary diseases as part of pre-implantation diagnostic testing of biopsied blastomere cells (Kristianson et al., 1994, Snabes et al., 1994, van der Veyer et al., 1995), or as part of prenatal diagnostic testing of nucleated erythrocytes in maternal blood (Sekizawa et al., 1996).

According to the prior art, WGA is usually used to analyze microsatellites in tumor biopsies to detect microsatellite instability or the loss of heterozygosity. According to the prior art, the analyzed sample must contain so many cells, however, that a quantitatively disproportionate amplification of individual alleles caused by accidental preparation artifacts is ruled out (Zhang et al., 1992, Barret et al., 1995, Cheung and Nelson, 1996, Faulkner and Leigh, 1998). For instance, a batch of about 1,000 cells was investigated in a microsatellite analysis of FACS-sorted aneuploidal esophageal tumor cells (Barret et al., 1995).

In contrast to conventional in situ hybridization (Van Ommen et al., 1995) or conventional, specific PCR (Becker et al., 1996), multiple analyses of the same sample can be carried out using WGA methods. Two different methods are used. In "degenerate oligonucleotide primer PCR" (DOP-PCR), amplification primers with defined sequences on the 5' and 3' ends and a randomized hexamer region in the middle of the primer are used (Telenius et al., 1992). Starting with only slightly stringent conditions in the first 5 thermal cycles, the next 35 thermal cycles are carried out under more stringent conditions at a higher annealing temperature so that, during these cycles, only completely complementary primers can bind to the DNA to be amplified. These methods are used, for instance, as the first step before performing an in situ hybridization with flow-sorted chromosomes (Blennow et al., 1992; Telenius et al., 1992; Kallionemie et al., 1994), or to perform comparative genomic hybridization (CGH) (Du-Manoir et al., 1993; Schlegel et al., 1995).

An alternative principle of WGA is "primer-extension preamplification" (PEP-PCR, Zhang et al., 1992). In contrast to the DOP-PCR, this method uses completely randomized 15-mer amplification primers. During 50 consecutive thermal cycles, denaturing is first carried out at 92° C., followed by hybridization under only slightly stringent temperature conditions at 37° C. This temperature is increased successively to 55° C. at a rate of about 0.1° C./second. At this temperature, the polymerase extension reaction takes place for another 4 minutes.

All methods known in the prior art (von Eggeling and Spielvogel, 1995) have the disadvantage of insufficient sensitivity, however, because a relatively large number of cells must be used to increase the possibility of obtaining an amplification product. In addition, the sensitivity of the assay is reduced even more as the length of the fragment to be amplified increases. For this reason, the methods known in the prior art had only been used in the amplification of relatively small fragments with a length of up to 580 base pairs (Snabes et al., 1994).

Another main disadvantage of the PEP-PCR known in the prior art lies in the fact that a convincing DNA mutation analysis has never been reliably carried out due to the inherent error rate of the Taq polymerase used. The error rate is due to the fact that using Taq polymerase during amplification leads to AT/GC transitions in the amplification product (Keohvong and Thily, 1989). In addition, deletion mutations may arise when Taq polymerase is used if the DNA to be amplified is capable of forming secondary structures (Carriello et al., 1991). The risk of obtaining amplification artifacts is especially high with WGA, however, because more than 80 amplification cycles are usually carried out during the 2 to 3 amplification reactions.

To avoid sequence artifacts during nucleic acid amplification, the use of DNA polymerases with 3'–5' exonuclease activity was also known in the prior art (Flaman et al., 1994; Casas and Kirkpontrick, 1996). The use of polymerases without 3'–5' exonuclease activity for WGA, however, leads to a further reduction in the sensitivity of the method, because such polymerases possess much less processivity than Taq DNA polymerases, for instance. As a result, the products created during preamplification when randomized primers are used are not long enough to serve as matrices for the subsequent specific PCR reaction if the fragment to be amplified exceeds a certain size.

The technical object to be solved with this invention was therefore to develop a method with which, starting with the smallest possible number of cells, specific nucleic acid fragments of high quality, i.e., containing no sequence artifacts, could be amplified and then analyzed. The quality of the amplification products should make it possible to carry out reliable mutation analyses, sequence analyses, and unequivocally interpretable microsatellite analyses. This objective is solved by an improved method of primer-extension preamplification (PEP-PCR, Zhang et al., 1992).

SUMMARY OF THE INVENTION

Object of the invention is therefore a method for the amplification of nucleic acid fragments from a sample comprising two or three thermocyclic amplification reactions in which completely randomized primers are used in the first amplification reaction and specific primers are used in the second amplification reaction, characterized in that, to amplify the DNA, a mixture of at least two DNA polymerases is used, at least one of which possesses 3'–5' exonuclease activity. This characteristic is also called proof-reading activity in the context of polymerases (Flaman et al., 1994).

An amplification reaction comprises about 20 to 60 thermal cycles. The first amplification reaction preferably comprises at least 40 thermal cycles and, most preferably, at least 50 thermal cycles. The second amplification reaction preferably comprises at least 30 thermal cycles, and most preferably, at least 40 thermal cycles.

Each thermal cycle comprises a denaturing phase, an annealing phase, and at least one elongation phase. Denaturation into single strands preferably takes place at temperatures of between 90° C. and 96° C. The annealing phase to hybridize the primers with the target nucleic acid preferably takes place at temperatures of between 30° C. and 50° C. Most preferably, the annealing phase takes place at temperatures of between 35° C. and 45° C. During the first amplification reaction, the annealing phase most preferably takes place at about 37° C. The elongation phase is carried out at temperatures of between 50° C. and 75° C. In a preferred embodiment, the elongation phase of the first amplification reaction takes place at temperatures of between 50° C. and 60° C. A temperature of about 55° C. is especially preferred.

An advantage of the embodiment of the invention claimed is a slow transition between the annealing phase and the elongation phase. This transition is carried out at a speed of less than 0.5° C. per second. It is most advantageous for the temperature transition to be carried out at a speed of 0.1 ° C./second.

To perform the method provided by this invention, it is advantageous for the elongation to be carried out during the first amplification reaction in the majority of cycles using two or more elongation steps, with one elongation carried out at a lower temperature and then continuing the elongation at a higher temperature. Using this approach, populations of especially long amplicons are created during the first amplification reaction. In this embodiment, the first amplification reaction preferably takes place at about 55° C., and the second amplification reaction takes place at about 65° C. to 72° C. A temperature of about 68° C. is optimal.

The primers used in the first amplification reaction are completely randomized, i.e., a population of single-stranded oligonucleotides is used in which every single nucleotide on every single position can comprise one of four nucleotide components A, T, G, or C. These primers are preferably 10–20 nucleotides long. Most preferably, the primers are about 15 nucleotides long. The specific primers used in the second amplification reaction are characterized in that they have a sequence that is identical to a sequence of the target nucleic acid or its complementary sequence over a range of at least 10 nucleotides. The specific primers used to carry out a "nested PCR" in a potential third amplification reaction are selected according to the same criteria as the primers used in the second amplification reaction. The sequences of the primers used that are identical to the target nucleic acid or its complement must be a component of the sequence amplified in the second amplification reaction.

The mixture of DNA polymerases provided by the invention preferably contains a thermostable DNA polymerase without 3'–5' exonuclease activity such as Taq DNA polymerase, for instance, and another thermostable DNA polymerase with 3'–5' exonuclease activity, such as Pwo DNA polymerase obtained from Pyrokokkus woesii (Boehringer Mannheim order no. 1644947). Other DNA polymerases without 3'–5' exonuclease activity can also be used as a component of the polymerase mixture.

One of the embodiments of the method claimed is a method for DNA amplification. To ensure the sensitivity of detecting certain sequences, it is advantageous to carry out the cell analysis of the material to be analyzed using enzymatic protease digestion to obtain the sample DNA. Proteinase K can be used, for instance.

In another embodiment of the method claimed, RNA is first isolated from the physical material to be analyzed. The sample of physical material can comprise one cell, fewer than 10 cells, or fewer than 100 cells. To obtain RNA, it is preferable to use chemical lysis using buffers that contain guanidinum isothiocynate. A corresponding cDNA is then created using a reverse transcriptase reaction. This cDNA is then used as the starting material for the primer-extension preamplification provided by this invention. The cDNA is preferably obtained via reverse transcription of poly-A RNA.

The methods claimed are suitable for use in analyzing samples from physical material that comprises just one or a few cells. The method claimed is therefore especially well-suited for use in analyzing nucleic acids from tissue slices. Such tissue slices can be obtained from frozen, formalin-fixed, or paraffin-embedded material. An appropriate protease digestion step is especially advantageous for these embodiments.

The use of polymerase mixtures in the primer-extension preamplification PCR provided by this invention leads to a surprisingly high sensitivity of DNA detection that cannot be achieved using the methods known from the prior art. Object of the invention is therefore a method for the amplification of nucleic acid fragments comprising two or three thermocyclic amplification reactions. Completely randomized primers are used in the first amplification reaction and specific primers are used in the second amplification reaction. In addition, the sample contains a quantity of nucleic acid corresponding to an equivalent of no more than 100 cells. This invention is characterized in that the likelihood of the amplificates forming is greater than 90%. Object of the invention are especially methods with which the likelihood is greater than 90% that amplificates will form from an equivalent of no more than 5–10 cells. In a special embodiment, the likelihood of amplificates forming from the equivalent of one cell is greater than 50%.

The method provided by the invention is suitable for use in the amplification of nucleic acid fragments having a length between 100 and 1000 base pairs. The method is especially suited for use in the amplification of nucleic acid fragments having a length between 150 and 550 base pairs.

In summary, the method provided by the invention makes it possible to amplify specific DNA fragments from nucleic acid samples obtained from just one or a few cells while ruling out or at least minimizing the creation of amplification artifacts. Object of the invention therefore also includes the use of DNA amplified according to the invention in mutation analysis. The mutation analysis can be carried out in a special embodiment in that the nucleic acid fragment amplified according to the invention is analyzed using a sequencing reaction.

Object of the invention claimed is also the use of DNA amplified according to the invention to analyze microsatellites, and especially to analyze nucleic acid samples obtained from frozen, formalin-fixed, or paraffin-embedded tissue slices. Cell equivalents of 5–20 cells are preferably used in this embodiment, because an even amplification of alleles from the same gene locus is not ensured if smaller quantities of cells are used. The analysis of microsatellites according to the invention can be used to diagnose microsatellite instability and the loss of heterozygosity (Boehm and Wieland, 1997).

In addition, when the equivalent of at least 10 cells is used, the likelihood of obtaining amplification products of both alleles is greater than 90%.

DETAILED DESCRIPTION OF THE INVENTION

EXAMPLE 1

Figure 1:
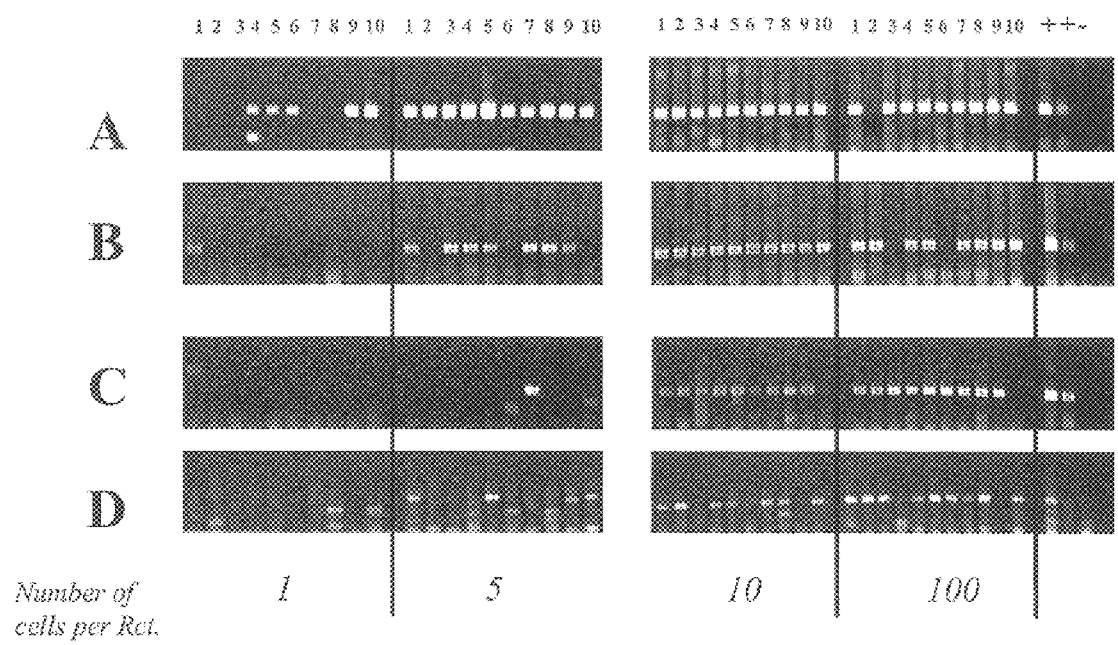
FIG. 1. Amplification of a 536-bp fragment of the β-globin gene from FACS-sorted SW480 cells. Ten assays each were carried out with 1, 5, 10, and 100 cells.
Row A: An Expand polymerase mixture used after lysis with proteinase K
Row B: Taq polymerase used after lysis with proteinaseK
Row C: Previously-known PEP-PCR after alkaline lysis
Row D: DOP-PCR FIG. 2. Microdissected material from frozen tissue slices of a bladder carcinoma biopsy in aliquots of about 50, 100, 200, 500, or 1000 cells. Amplification of a 536-bp fragment after lysis with proteinase K (A) or using Taq polymerase after alkaline lysis (B).

Sensitivity of Primer-Extension Preamplification According to the Invention

To compare the method provided by the invention and the methods known from the prior art, cells from the SW480 tumor cell line (ATCC) were separated using flow-through cytometry in equivalents comprising 1, 5, 10, or 100 cells. For this purpose, the cells were resuspended in PBS buffer containing 0.1 µg/ml fluorescein diacetate and incubated in it for 5 minutes. The lipophilic, non-fluorescent fluorescein diacetate diffuses through the cell membrane and is then hydrolyzed intracellularly by non-specific esterases, producing negative-charged fluorescein that cannot diffuse (Endl et al., 1996, Dive et al., 1990, Ross et al., 1989). The fluorescence measurements were carried out with an FACStarplus cell sorter (Becton-Dickinson). To do this, the fluorescence was excited using a water-cooled argon ion laser at a wavelength of 488 nm. The emission was detected on the FL 1 channel using a 525-nm band pass filter with a band width of 30 nm. The sorting was set using 20 fluorescein-labelled microbeads (Polysciences, Carboxy YG 4.5, Warrington). The procedures were carried out three times, and the beads were then counted under a fluorescent microscope. Sorting was considered to be correct if all three sorting procedures produced a result of 20 microbeads. Cell analysis was carried out at a speed of about 200 cells per second. Cell sorting was carried out with drop feed speed of 25,000 Hz directly into Eppendorf vessels that already contained the lysis buffer used. This procedure was used to make 40 aliquots of 1, 5, 10, or 100 cells each.

Cell lysis was carried out according to the invention in 10 µl High Fidelity buffer (50 mM Tris-HCL, 22 mM $(NH_4)_2SO_4$ 2.5 mM $MgCl_2$, pH 8.9) which also contained 4 mg/ml proteinase K and 0.5 vol % Tween 20 (Merck) for 12 hours at 48° C. The enzyme was then inactivated for 15 minutes at 94° C. Lysis was performed in parallel batches according to the prior art (Zhang et al. 1992) in 5 µl, 200 mM KOH, 50 mM dithiothreitol for 10 minutes at 65°. The batches were then neutralized with 5 µl 900 mM TrisHCl pH 8.3, 300 mM KCl. Preamplication as provided by the invention was then carried out for 10 samples each using completely randomized 15-mer primers (16 µM) and dNTP (100 µM) with 5 units of a mixture of Taq polymerase (Boehringer Mannheim) and Pwo polymerase (Boehringer Mannheim) in a ratio of 10:1 under standard PCR buffer conditions (50 mM Tris-HCL, 22 mM $(NH_4)_2 SO_4$, 2.5 mM $Mgll_2$, pH 8.9, also containing 0.05 mg/ml gelatine) in a total volume of 60 µl with the following 50 thermal cycles:

| Step | Temperature | Time |
|------|-------------|------|
| 1 | 92° C. | 1' 30" |
| 2 | 92° C. | 40" |
| 3 | 37° C. | 2; |
| 4 | ramp: | 0.1° C./sec to 55° C. |
| 5 | 55° C. | 4' |
| 6 | 68° C. | 30" |
| 7 | go to step 2, 49 times | |
| 8 | 8° C. | 15' |

Preamplification was also carried out with the following 50 thermal cycles:

| Step | Temperature | Time |
|------|-------------|------|
| 1 | 94° C. | 4' |
| 2 | 94° C. | 30" |
| 3 | 32° C. | 1' |
| 4 | ramp: | 0.1° C./sec to 55° C. |
| 5 | 55° C. | 45" |
| 6 | go to step 2, 19 times | |
| 7 | 94° C. | 30" |
| 8 | 60° | 45" |
| 9 | ramp: | 1° C./sec to 72° C. |
| 10 | 72° C. | 1' |
| 11 | go to step 7 29 times | |
| 12 | 72° C. | 8 min |
| 13 | 4° C. | undefined |

In this embodiment, the gelatins were also replaced with 5 vol % DMSO.

In control expriments, 5 units of Taq polymerase (Life Technologies) were used according to the prior art instead of the polymerase mixture according to this invention. The samples used had been obtained either via alkaline lysis or enzymatic lysis. In another control experiment, a DOP-PCR was carried out after enzymatic proteinase K digestion using the DOP-PCR master kit (Boehringer Mannheim) in accordance with the manufacturer's instructions.

In a second amplification round, a tenth of an aliquot (6 µl) was specifically amplified after addition of 0.5 µM each of primers with sequence ID no. 1 and 2, a 536-bp fragment of the β-globin gene in the presence of 0.2 mM dNTP, and 0.5 µl of the sample polymerase that was used in the first amplification round. The aliquot was specifically amplified in a total volume of 20 µl under PCR standard buffer conditions (High Fidelity 50 mM Tris-HCL pH 8.9, 22 mM $(NH_4)_2 SO_4$, 1.5 mM Mg $Cl_2$) using the following thermal cycles:

| | | |
|---|---|---|
| 94° C. | 3 min | |
| 94° C. | 1 min | |
| 60° C. | 1 min | } 50× |
| 72° C. | 1 min | |
| 72° C. | 10 min | |

The amplification products were then analyzed on agarose gel stained with 2% ethidium bromide. As shown in FIG. 1, preamplification according to the invention is clearly superior to the PEP-PCR and DOP-PCR methods in terms of sensitivity in the amplification of a 536-Bp β-globin fragment. In the single cell assays, a specific amplification product was obtained in more than 50% of the cells investigated using the polymerase mixture according to the invention after enzymatic lysis. None of the other methods generated any amplification product.

In assays with 5 (or more) cells, the use of the polymerase mixture after enzymatic lysis yielded an amplification product in every sample tested. The use of Taq polymerase instead of the polymerase mixture resulted in amplification product in 70% of the 5-cell assays. In contrast, using the DOP-PCR or preamplification methods known from the prior art, i.e., using Taq polymerase after alkaline lysis, lead to amplification products in a minority of the cell populations tested.

This demonstrates that the use of a polymerase mixture for preamplication according to the invention that comprises polymerase with proofreading activity (3'–5' exonuclease) and a polymerase without proofreading activity is advantageous in the analysis of the smallest cell populations, all the way down to single cells, because using it is very likely to result in a specific amplification product. This significantly increases the sensitivity of such assays. The experiment also demonstrates that performing enzymatic cell lysis instead of alkaline lysis is advantageous for the corresponding assays.

EXAMPLE 2

Preamplification of Cell Material Obtained from Frozen Tissue Slices

Figure 2:
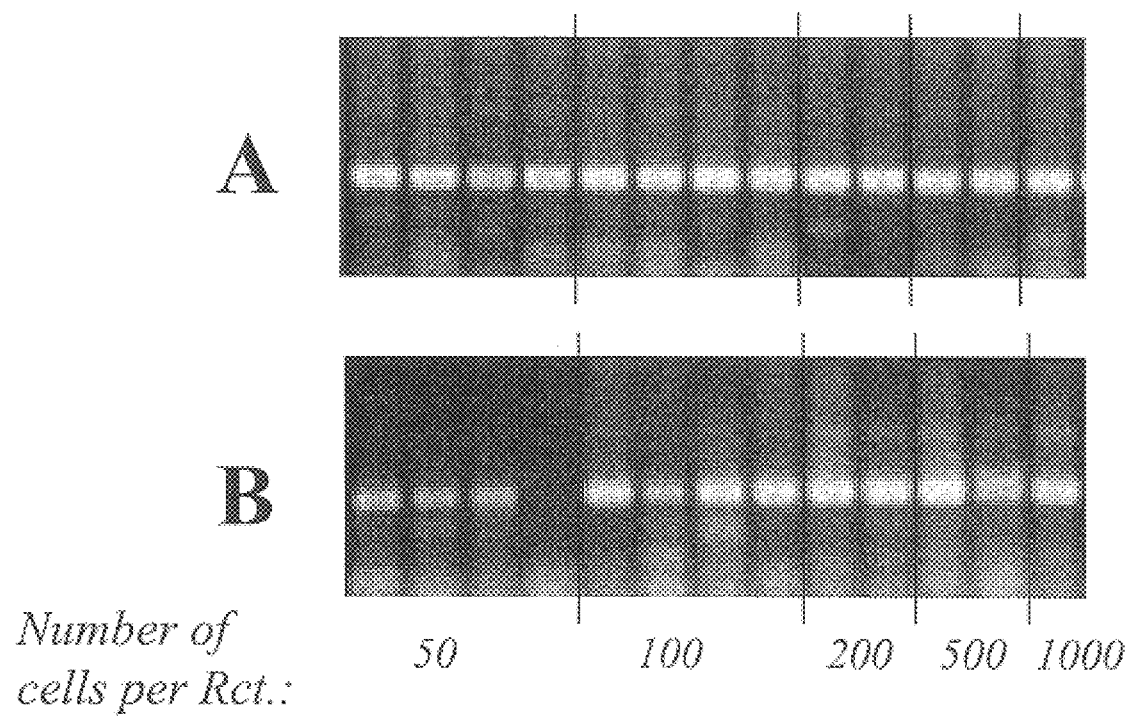

Frozen tissue slices (5 µm thick) were made from a bladder biopsy and stained with methylene blue (Romeis, 1989). These slices were microdissected into sections containing about 50, 100, 200, 500 or 1000 cells. Microdissection was performed manually using a micromanipulator (Leitz; serial no. 980629) and an inverted light microscope (Leitz, Labovert FS) enlarged 400 times. A 536-Bp β-globin fragment was then preamplified/amplified as described in Example 1. As shown in FIG. 2, saturated amplification took place in all aliquots analyzed if preamplification is carried out according to the invention, i.e., using an Expand polymerase mixture after lysis with proteinase K. In contrast, saturated amplification products were obtained using Taq polymerase after alkaline lysis only if aliquots of at least 200 microdissected cells were used.

EXAMPLE 3

Sensitivity of Microsatellite Analysis of a Tumor Cell Line

Cells from the SW480 cell line(ATCC) were separated into 10 aliquots each of 1, 5, 10, or 100 cells according to the method described in Example 1. Preamplification with an Expand polymerase mixture was carried out according to the invention as described in Example 1 after enzymatic lysis with proteinase K.

After preamplification, 1/30 aliquots were used in the analysis of microsatellite locus D2S123. For the amplification, 0.3 µM primer with sequence ID nos. 3 and 4 were used under standard PCR conditions (Dietmaier et al., 1997). The PCR amplifications were carried out as follows in a volume of 20 µl:

Denaturing: 94° C. 1 Minute
Annealing: 60° C. 1 Minute
Elongation: 72° C. 1 Minute After being repeated 50 times, the last elongation step was carried out at 72° C. for 8 minutes.

3 µl sample buffer (96% formamide, 1% xylene cyanol ff, 1% bromophenol blue, 10 mMol EDTA pH 8.0) were added to 3 µl of the PCR product. The mixture was denatured for 4 minutes at 94° C. and separated using gel electrophoresis on a 6.7% polyacrylamide/50% urea gel for 1 hour at 1,500 volts and 50° C. in a sequencing gel chamber (Biorad).

Figure 3:
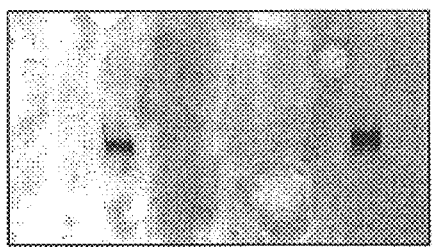
FIG. 3. Microsatellite analysis of locus D2S 123 of cell line SW480 with 10 samples each, containing 1, 5, 10, or 100 Zellen.
Figure 3:
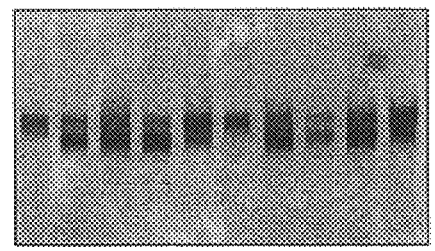
Figure 3:
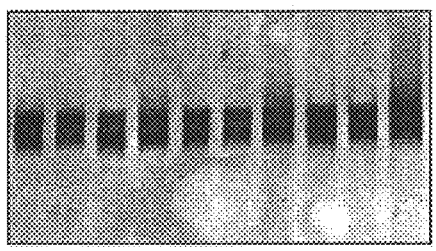
Figure 3:
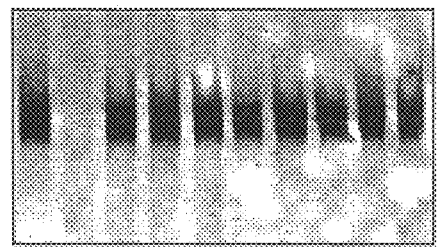

As shown in FIG. 3, the cells of the microsatellite-stable SW480 cell line exhibited a uniform type of allele. It was possible to detect both alleles reliably when at least 10 cells were used. In a 5-cell assay, both alleles could still be detected with about 80% certainty. In the single-cell assay, on the other hand, single alleles could rarely be detected.

EXAMPLE 4

Microsatellite Analysis of Material Obtained From Frozen Tissue Slices

Figure 4:
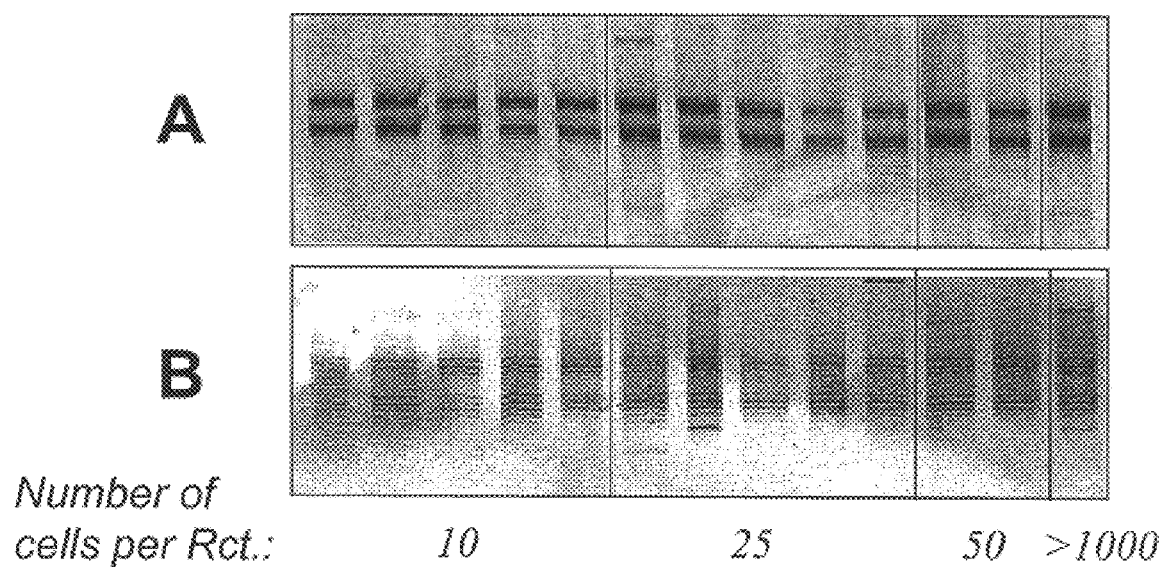
FIG. 4. Microsatellite analysis of locus D2S123 from microdissected frozen tissue slices of a bladder carcinoma biopsy on aliquots of about 10, 25, 50, or more than 1,000 cells each.
Upper gel row A: Preamplification according to the invention after enzymatic lysis with an Expand polymerase mixture.
Lower gel row B: Preamplification with Taq polymerase after alkaline lysis.

In another experiment, a row of microdissected cells from a bladder tumor biopsy was separated similar to Example 2 in equivalents of about 10, 25, 50, and 1,000 cells and either alkaline-lysed or lysed with proteinase K. The lysates were then used similar to Example 3 in a microsatellite analysis of the D2S123 locus. As shown in FIG. 4, an equivalent of just 10 cells is sufficient to reliably obtain allele-specific amplification products when performing a preamplification PCR according to the invention, i.e., with enzymatic lysis using proteinase K and using an enzyme mixture of Taq polymerase and Pwo polymerase. Both alleles are represented evenly and create a distinct band pattern that can be evaluated. In contrast, the method of alkaline lysis followed by preamplification using Taq polymerase as described in the prior art produced diffuse band patterns in the analysis of about 10 cell equivalents that could not be unequivocally evaluated.

EXAMPLE 5

Microsatellite Analysis of Paraffin-Embedded Tissue

Figure 5:
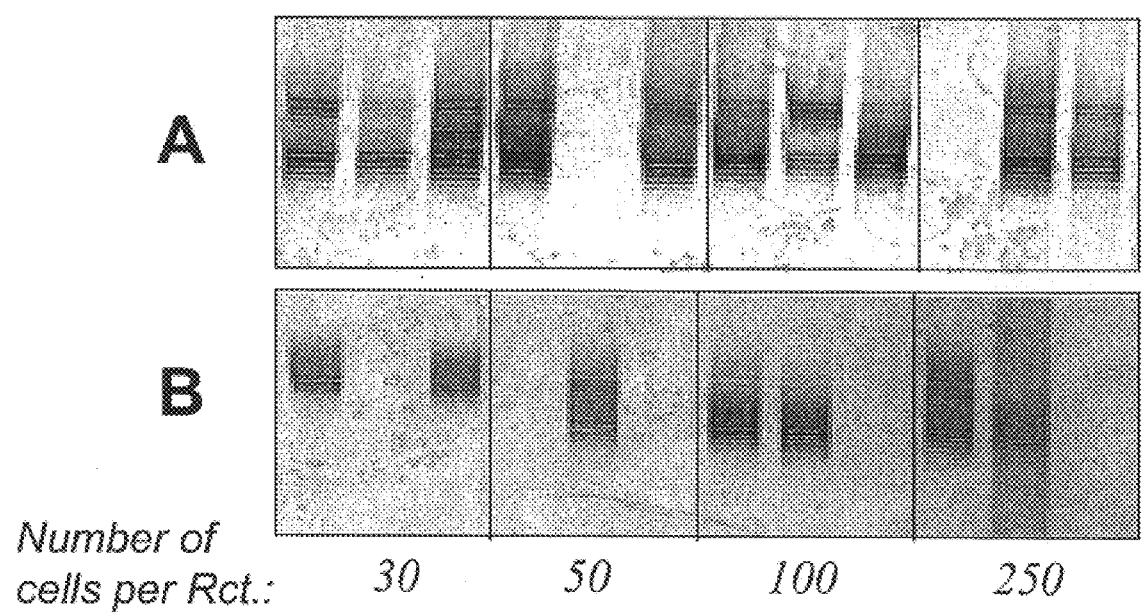
FIG. 5. Microsatellite analysis of locus D2S123 from microdissected slices of a colon carcinoma biopsy that were affixed in formalin and embedded in paraffin on aliquots of about 30, 50, 100, or 250 cells each.
Upper gel row A: Preamplification according to the invention after enzymatic lysis with an Expand polymerase mixture.
Lower gel row B: Preamplification with Taq polymerase after alkaline lysis.
Figure 6:
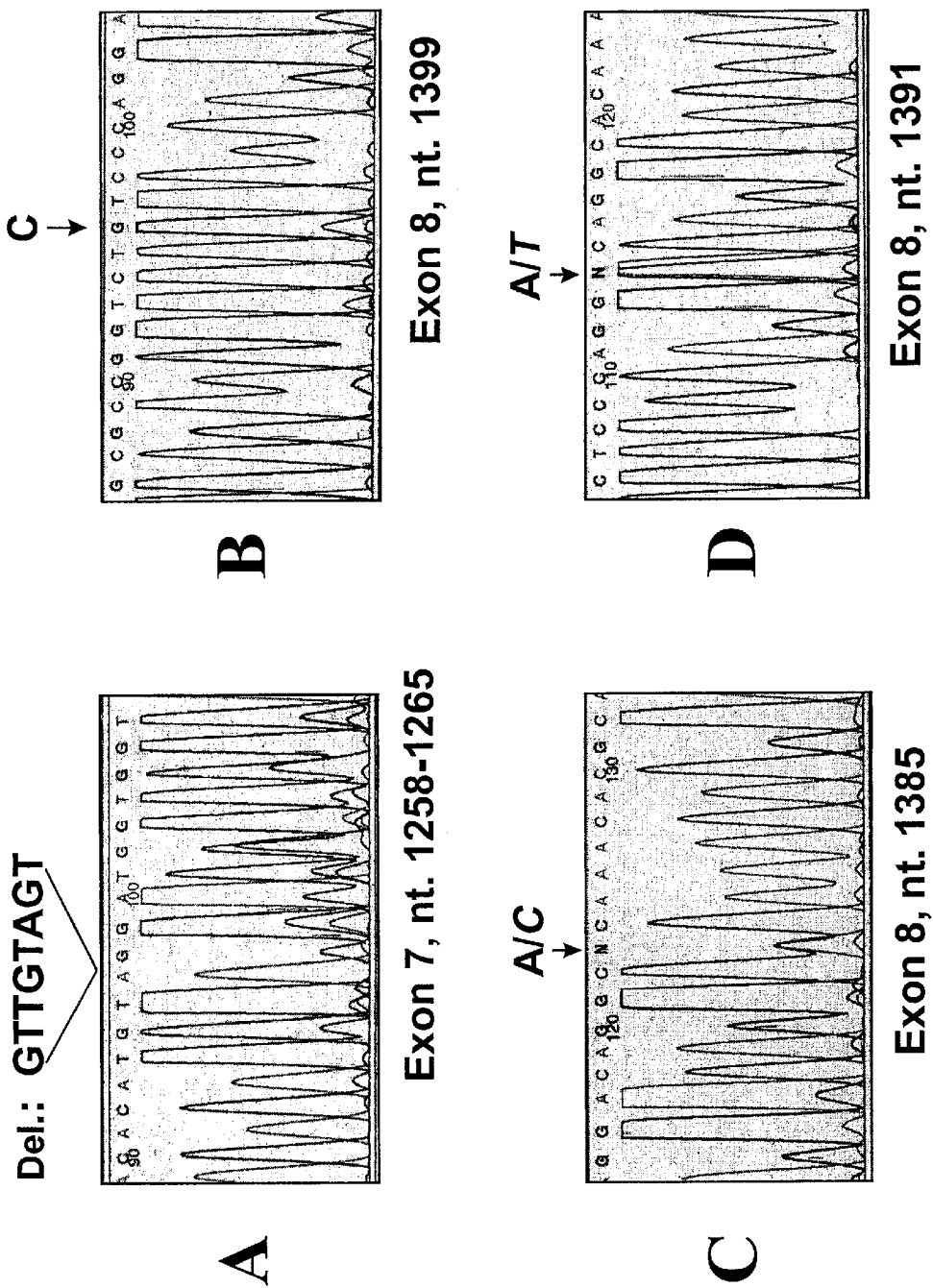
FIGS. 6A–6D Mutation analysis of the P53 gene using DNA from breast carcinoma biopsies that was preamplified according to the invention.

Colon carcinoma tissue was stained with hematoxilin/eosin (Romers, 1989, p 213), affixed in PBS-buffered formalin (formalin: 3.7% formaldehyde in PBS) for 14 h, embedded in paraffin, and then cut into 5-µm slices and placed on microscope slides. To destain, the microscope slides were washed for 2*15 min. in xylene, 2*10 min. in 99.9% ethanol, 2*10 min. in 96% ethanol, and 2*10 min. in 70% ethanol. After microdissection into about 30, 50, 100 and 250 cells, a microsatellite analysis was performed as described in Example 4. As shown in FIG. 5, evaluateable allele-specific amplification products with even representation of both alleles were obtained in the analysis of an equivalent of 30 cells by performing a preamplification PCR according to the invention, i.e., using enzymatic lysis with proteinase K and using an enzyme mixture of Taq polymerase and Pwo polymerase. In contrast, the method of alkaline lysis followed by preamplification using Taq polymerase as described in the prior art led to diffuse band patterns that often represented only single alleles.

EXAMPLE 6

P53 Mutation Analysis

To determine the error rate of the method of improved PEP-PCR followed by gene-specific PCR amplification, genomic regions of the P53 gene (exon 7 and exon 8) and 8 different breast carcinoma were analyzed. To accomplish this, "touch preparations" (Kovach et al., 1991) were made. Similar to Example 2, cell clusters of about 50–60 cells were microdissected and then enzymatically lysed and preamplified according to the invention. A P53-specific PCR was then carried out. As a control reaction, non-preamplified DNA was amplified under the same conditions. The specific amplification was carried out under standard conditions in a reaction volume of 50 µl (200 nM dNTPs, 1.25 U Expand polymerase (Boehringer Mannheim), 1.5 mM (exon 7) and 2 mM (exon 8) MgCl$_2$, and 0.4 µM each of the amplification primers with the following thermal cycles:

| | | |
|---|---|---|
| 1× | 94° C. | 2 min |
| 35× | 94° C. | 1 min |
| | 50° C. | 2 min |
| | 72° C. | 3 min |
| 1× | 72° C. | 10 min |

2 µl of the first PCR reaction were used for a necessary nested PCR. The following primers were used in various amplification reactions:

```
Seq. ID No. 5   Exon7 first round up     5'AAAGGCCTCCCCTGCT 3'

Seq. ID No. 6   Exon7 first round down   5'GAGCAGTAAGGAGATT 3'

Seq. ID No. 7   Exon7 sec. round up      5'CTCCCCTGCTTGCCA 3'

Seq. ID No. 8   Exon7 sec. round down    5'GATGGGTAGTAGTATG 3'

Seq. ID No. 9   Exon8 first round up     5'GACAGGTAGACCTGAT 3'

Seq. ID No. 10  Exon8 first round down   5'TCTGAGGCATAACTGC 3'

Seq. ID No. 11  Exon8 sec. round up      5'AGACCTGATTTCCTTAC 3'

Seq. ID No. 12  Exon8 sec. round down    5'TAACTGCACCCTTGGTC 3'
```

The amplification products were sequenced with the cycle-sequencing method using the "PRISM Ready Dye Terminator Sequencing Kit" and AmpliTaqFS polymerase (Applied Biosystems). To accomplish this, the amplified DNA fragments were first precipitated with polyethylene glycol. 3.2 pmol of a sequencing primer (Seq. ID No. 5–12) and 8.0 µl premix containing buffer, stain-labelled ddNTPs, dNTPs, and Ampli-Taq FS/pyrophosphatase were added to 50–150 ng of the precipitate. After denaturing at 96° C. for 2 min., the reactions were incubated over 25 cycles as follows:

96° C./15 sec., 50° C./15 sec., 60° C./4 min.

The samples were then ethanol-precipated, dried, and resuspended in 2 μl sample buffer (5:1 deionized formamide, 0.05 Mol EDTA, pH 8), heated to 92° C. for 2 minutes, then loaded onto an Applied Biosystem 373 sequencing unit.

A comparison of the sequence analyses of DNA preamplified according to the invention with DNA from the same patient that was used directly in the sequencing revealed no difference in any of the patients investigated. The position and type of mutations identified are shown in FIGS. 6A–6D as an example. FIGS. 6A–6D shows a heterozygotic 8-base pair deletion in exon 7 (6a), a hemozygotic CIG-G/C transversion (6b), a heterozygotic A/T-/C/G transversion (6c), and a heterozygotic A/T-T/A transversion in exon 8 (6d) after primer-extension preamplification according to the invention. No further mutations were found. This means that preamplication according to the invention with an enzyme mixture of Taq polymerase and a polymerase with proof-reading activity not only leads to increased sensitivity of amplification reactions and microsatellite analyses, but also that the amplification products exhibit no errors in their sequence and can therefore be used in mutation analysis.

EXAMPLE 7

Analysis of Disseminated Tumor Cells with RFLP Using Ki-ras as an Example 10 ml of punctured bone marrow aspirate from pancreatic tumor patients or colon cancer patients were purified in a Ficoll density gradient. A total of $2 \times 10^6$ bone marrow cells were immunohistochemically stained with an anti-CK18 antibody (CK2 clone, Boehringer Mannheim) according to the manufacturer's instructions. CK 18-positive cells were microdissected as single cells or in clusters with very low cell counts of cytospots using a laser microdissector (Schütze, 1994). The enzymatic lysis was carried out using proteinase K according to the invention and as described in Example 1, and preamplification was carried out using a mixture of Taq polymerase and Pwo polymerase (10:1 mixing ratio).

The analysis of the restriction fragment length polymorphism was carried out according to Trumper's protocol using the enrichment PCR (Trumper et al., 1994): to accomplish this, a 157-bp fragment of the Ki-ras gene was amplified from a tenth of the batch of a preamplification PCR according to the invention with 0.5 μM each of primers 5'BstNI (Seq. ID No. 13) and 3'WT (Seq. ID No. 14) in a volume of 50 μl in 16 thermal cycles at an annealing temperature of 57° C. with 1 U and Expand HiFi polymerase. A 16 μl-aliquot was then digested in a volume of 20 μl with 20 U MvaI (BstNI isoschizomer). 20 μl of MvaI-digested fragment and 10 μl of undigested fragment were amplified in a second PCR using 0.5 μM each of 5'BstNI primer and 3+BstNI primer (Seq. ID No. 15) in a total volume of 50 μl during 35 thermal cycles at an annealing temperature of 60° C. 30 μl of the batch were then digested with MvaI and, after addition of 7 μl of non-denatured sample buffer, it was analyzed using gel electrophoresis on a non-denatured 10% polyacrylamide gel.

Figure 7:
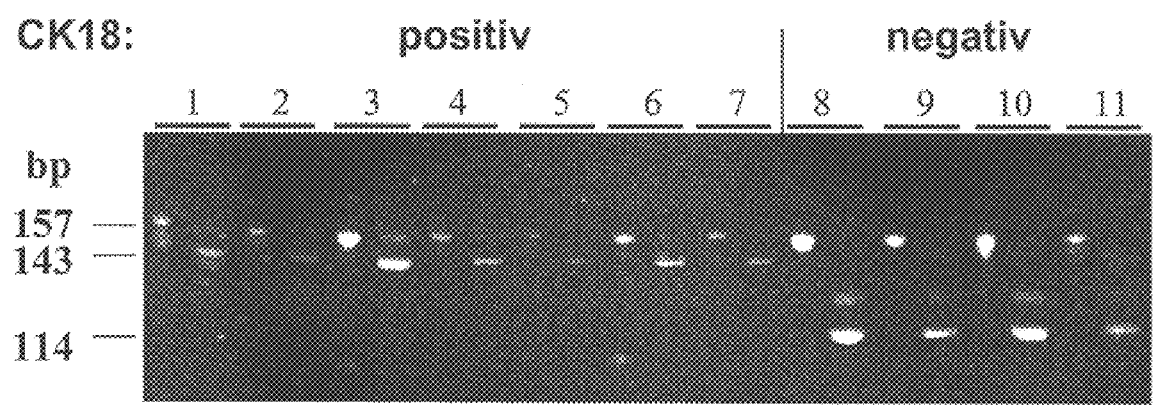
FIG. 7. Detection of Ki-ras mutations on CK18-stained, disseminated tumor cells from bone marrow using RFLP. In each case, the DNA was applied in parallel undigested and digested with Mval.
Lanes 1,2,: Immuncytochemically CK18-positive single cells from a patient with pancreatic cancer
Lanes 4,5: Immuncytochemically CK18-positive single cells from a patient with colon cancer
Lane 3,6,7: A few immuncytochemically CK18-positive cells from a patient with colon cancer
Lanes 8–11: About 100 unstained, hematopoietic stem cells each as negative controls FIG. 8. Amplification of a 408-Bp fragment of the β2-microglobulin gene using cDNA isolated from single cells.
Upper gel: Lane 1: Size marker, HindIII-digested Lambda DNA; Lanes 2 to 13: preamplification PCR according to the invention from 12 different single cells; Lane 14: positive control using cDNA from 5,000 cells preamplified according to the invention; Lane 15: positive control with 1 µg cDNA amplified according to the invention; Lane 16: positive control with 1 µg of non-preamplified cDNA; Lane 17: negative control without reverse transcriptase during reverse transcription; Lane 18: negative control without using cDNA during preamplification.
Lower gel: Lane 1: Size marker, HindIII-digested Lambda DNA; Lanes 2 to 13: 1/10 aliquots of non-preamplified cDNA from various single cells; Lane 14: positive control with 1 µg of non-preamplified cDNA.
Figure 8:
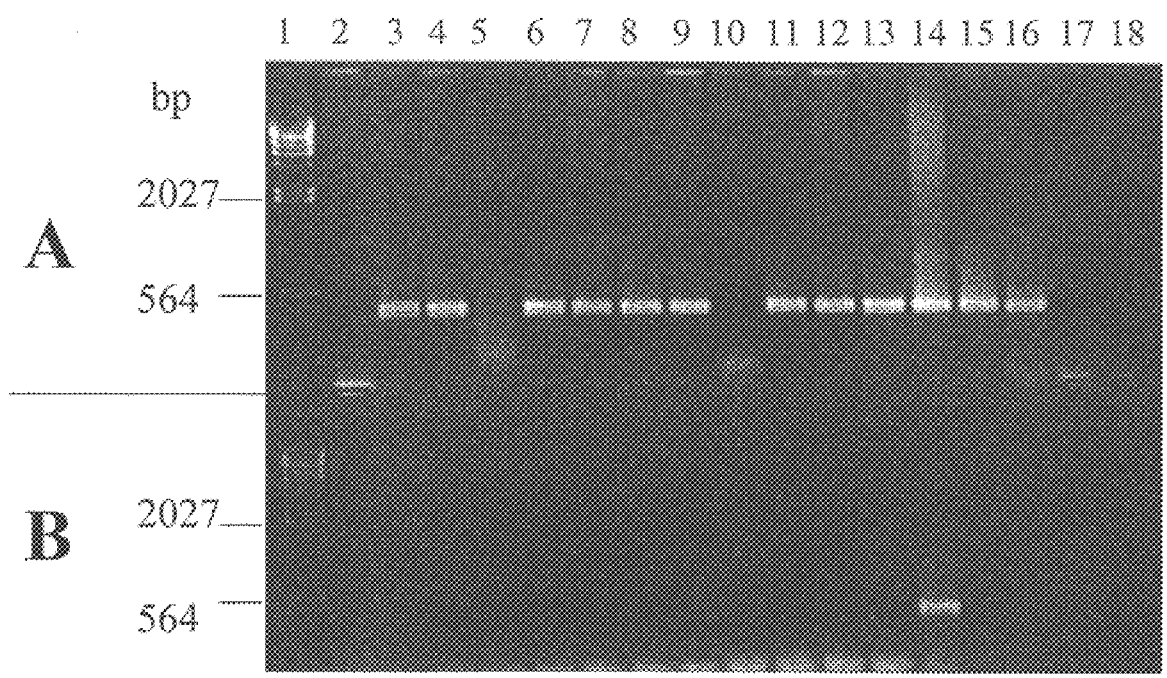

As shown in FIG. 7, DNA from all samples was successfully amplified. The existence of DNA fragments with a size of 143 bp after MvaI digestion is evidence of mutation in all the tumor material investigated (lanes 1–7). All control reactions carried out with DNA from cells that cannot be stained with anti-CK 18 (lanes 8–11), in contrast, result in a non-mutated 114-bp product. A method has therefore been developed for the first time with which numerous mutations can be diagnosed reliably and with a high rate of detection from individual, disseminated tumor cells.

EXAMPLE 8

Preamplification of Reverse-Transcribed RNA

Colorectal carcinoma cells from the Lovo (ATCC) cell line were separated using a fluorescence-activated cell sorter. Poly (A) RNA was isolated from the individual cells using the Dynabead mRNA Direct Kit (Dynal, Hamburg). The entire batch was reverse-transcribed (20 μl according to the manufacturer) using SuperScript RNaseH reverse transcriptase (Life Technologies) and oligo (dT) primers. The resultant cDNA (20 μl) was used as a template for preamplification according to the invention in accordance with the preamplification PCR protocol described in Example 1. 1/30 of the cDNA preamplified in this fashion was then used as the template for amplification of a specific 408-bp fragment of the β2-microglobulin gene. 1/10 aliquots each of the cDNA were used for amplification in a control reaction. The PCR was carried out under standard conditions at an annealing temperature of 60° C., 50 cycles, and in the presence of 0.2 mMol dNTP, 5 μMol PCR primers (Sequenz ID no. 16 and 17) and 0.54 units of Expand Hifi polymerase in a volume of 30 μl. As shown in FIG. 7, an amplification product was obtained from preamplified cDNA in 9 of 12 analyzed single cells, while the use of DNA that was preamplified not according to the invention did not result in any detectable amplification products.

REFERENCES

Abeln ECA, Corver W E, Kuipers-Dijkshoorn N J, Fleuren G J and Cornelisse C J (1994). Br J Cancer, 70, 255–262. Molecular genetic analysis of flow-sorted ovarian tumour cells: improved detection of loss of heterozygosity.

Barret M T, Galipeau P C, Sanchez C A, Emond M J and Reid B J. (1996). Oncogene, 12, 1873–1878. Determination of the frequency of loss of heterozygosity in esophageal adenocarcinoma by cell sorting, whole genome amplification and microsatellite polymorphisms.

Barret M T, Reid B J and Geoffrey J. (1995). Nucleic Acids Research, 23, 3488–3492. Genotypic analysis of multiple loci in somatic cells by whole genome amplification.

Becker I, Becker K-F, Röhrl M H, Minkus G, Schütze K, and Höfler, H. (1996). Lab Invest, 75, and 801–807. Single-cell mutation analysis of tumors from stained histologic slides.

Blennow E, Telenius H, Larsson C, de Vos D, Bajalica S, Ponder B A and Nordenskjold M (1992). Hum Genet, 90, 371–374. Complete characterization of a large marker chromosome by reverse and forward chromosome painting.

Böhm M, Wieland I, Schütze K and Rübben H. (1997). Am J Pathol, 15, 63–67. Microbeam MOMeNT. Non-contact laser microdissection of membrane-mounted native tissue.

Boehm M and Wieland I (1997). International J of Oncology, 10, 131–139. Analysis of tumor-specific alterations in native specimens by PCR: How to procure the tumour cells!

Casas E and Kirkpatrick B W. (1996). BioTechniques 20, 219–225. Evaluation of different amplification protocols for use in primer-extension preamplification.

Cheung V and Nelson S F (1996). Proc. Natl. Acad. Sci. USA, 93, 14676–14679. Whole genome amplification using a degenerate oligonucleotide primer allows hundreds of genotypes to be performed on less than one nanogram of genomic DNA.

Dietmaier W, Wallinger S, Bocker T, Kullmann F, Fishel, R, and Rüschoff J. (1997). Cancer Res., 57, 4749–4756. Diagnostic microsatellite instability: definition and correlation with mismatch repair protein expression.

Dive C, Watson J V and Workman P (1990). Cytometry 11, 244–252. Multiparametric Analysis of cell membrane permeability by two colour flow cytometry with complementary fluorescent probes.

du-Manoir S, Speicher M R, Joos S, Schrock E, Popp S, Dohner H, Kovacs G, Robert-Nicoud M, Lichter P, and Cremer T. (1993). Hum-Genet. 1993, 90, 590–610. Detection of complete and partial chromosome gains and losses by comparative genomic in situ hybridization.

Emmert-Buck M R, Bonner R F, Smith P D, Chuaqui R F, Zhuang Z, Goldstein S R, Weiss R A, and Liotta L A (1996). Science 274, 998–1001. Laser capture microdissection.

Emmert-Buck-M R; Roth-M J; Zhuang-Z; Campo-E; Rozhin-J; Sloane-B F; Liotta-L A; Stetler-Stevenson-W G (1994). Am J Pathol 145(6), 1285–1290. Increased gelatinase A (MMP-2) and cathepsin B activity in invasive tumor regions of human colon cancer samples.

Endl E, Steinbach P, Schärfe J, Fickweiler S, Wörle K, Hofstädter F (1996). Ultrasound. Med. Biol. 22, 515–525. Cell type specific response to shock waves of suspended or pelleted cells as analysed by flow cytometry or electrical cell volume determination.

Faulkner SW and Leigh A (1998). BioTechniques, 24, 47–50. Universal amplification of DNA from small regions of paraffin-embedded formalin-fixed tissue.

Flaman J M, Freborg T, Moreau V, Charbonnier F, Martin C, Ishioka C, Friend S H and Iggo R (1994). Nucl Acids Res, 22, 3259–3260. A rapid PCR fidelity assay.

Kallioniemi A, Kallioniemi O P, Sudar D, Rutovitz D, Gray J W, Waldman F and Pinkel D (1992). Science, 258, 818–821. Comparative genomic hybridization for molecular cytogenetic analysis of solid tumors.

Keohvong P and Thily W G (1989). Proc. Natl. Acad. Sci. USA, 86, 9253–9257. Fidelity of DNA polymerases in DNA amplification.

Kovach J S, R M McGovern, Cassady J D, Swanson S K, Wold L E, Vogelstein B and S S Sommer (1991). Journal of the National Cancer Institute, 83, 1004–1009. Direct sequencing from touch preparations of human carcinomas: Analysis of p53 mutations in breast carcinomas.

Kristjansson K, Chong S S, Van den Veyer I B, Subramanian S, Snabes M C and Hughes M R. (1994). Nature Genetics, 6, 19–23. Preimplantation single cell analyses of dystrophin gene deletions using whole genome amplification.

Noguchi S; Motomura K; Inaji H; Imaoka S; Koyama H (1994). Cancer Res 54, 1849–1853. Clonal analysis of predominantly intraductal carcinoma and precancerous lesions of the breast by means of polymerase chain reaction.

Romeis B. 17. (1998). Mikroskopische Technik. 17. Aufl. Urban and Schwarzenberg, 1989. S.213–232.

Ross D D, Joneckis C C, Ordonez J V, Sisk A M, Wu R K, Hamburger A W and Nora R E (1989). Cancer Res 49, 3776–3782. Estimation of cell survival by flow cytometric quantification of fluorescein diacetate/propidium iodide viable cell number.

Schütze K and Clement-Sengewald A (1994). Nature, 368, 667–669. Catch and move-cut or fuse.

Sekizawa A, Watanabe A, Kimura T, Saito H, Yanaihara T and Sato Takeshi. (1996). Obstetrics and Gynecology, 87 (4), 501–505. Prenatal diagnosis of the fetal RhD blood type using a single fetal nucleated erythrocyte from maternal blood.

Shibata D, Hawes D, Li Z H, Hernandez A M, Spruck C H and Nichols P. (1992). Am J Pathol, 141, 539–543. Specific genetic analysis of microscopic tissue after selective ultraviolet radiation fractionation and the polymerase chain reaction.

Shibata D. (1993). Am J Pathol, 143, 1523–1526. Selective ultraviolet radiation fractionation and polymerase chain reaction analysis of genetic alterations.

Snabes M C, Chong S S, Subramanian S B, Kristjansson K, DiSepio D and Hughes M R. (1994). Proc. Natl. Acad. Sci. USA, 91, 6181–6185.

Telenius H, Carter N P, Bebb C E, Nordenskjold M, Ponder B A and Tunnacliffe A (1992). Genomics. 1992, 13, 718–25. Degenerate oligonucleotide-primed PCR: general amplification of target DNA by a single degenerate primer.

Trümper L H, Büger B, von Bonin F, Hintze A, von Blohn G, Pfreundschuh M and Daus H. (1994). Br. J. Cancer, 70, 278–284. Diagnosis of pancreatic adenocarcinoma by polymerase chain reaction from pancreatic secretions.

Van den Veyer I B, Chong S S, Cota J M, Bennett P R, Fisk N M, Handyside A H, Cartron J-P, Le Van Kim C, Colin Y, Snabes M C, Moise K J, Hughes M R. (1995). Am J Obstet Gynecol, 172, 533–540. Single-cell analysis of the RhD blood type for use in preimplantation diagnosis in the prevention of severe hemolytic disease of the newborn.

Van Ommen G J, Breuning M H and Raap-A K (1995). Curr Opin Genet Dev, 5(3): 304–308. FISH in genome research and molecular diagnostics.

Von Eggeling F and Spielvogel H (1995). Cell and Mol Biology, 41(5), 653–670. Applications of random PCR.

Zhang L, Cui X, Schmitt K, Hubert R, Navidi W, and Amheim N (1992). Proc. Natl. Acad. Sci. USA, 89, 5847–5851. Whole genome amplification from a single cell: Implications for genetic analysis.

Zhuang Z, Bertheau P, Emmert-Buck M R, Liotta L A, Gnarra J, Linehan W M, Lubensky I A. (1995). Am J Pathol, 146, 620–625. A microdissection technique for archival DNA analysis of specific cell populations in lesions <1 mm in size.

We claim:

1. A method for the amplification of nucleic acid fragments from a sample of cells, said method comprising treating said sample of cells with a protease, followed by two thermocyclic amplification reactions, wherein first amplification reaction is carried out using completely randomized primers, second amplification reaction is carried out using specific primers, and said first and second amplification reactions are carried out using the same mixture of at least two DNA polymerases, at least one of which possesses 3'–5' exonuclease activity.

2. The method of claim 1, wherein, in said first amplification reaction, the temperature at which primer extension is carried out is increased in at least some of the successive amplification cycles.

3. The method of claim 1, wherein said mixture of DNA polymerases comprises a DNA polymerase without 3'–5' exonuclease activity and a DNA polymerase with 3'–5' exonuclease activity.

4. The method of claim 1, wherein said protease is proteinase K.

5. The method of claim 3, wherein said mixture of DNA polymerases comprises Taq DNA polymerase and Pwo DNA polymerase.

* * * * *